(12) United States Patent
Sweet et al.

(10) Patent No.: US 9,939,358 B2
(45) Date of Patent: Apr. 10, 2018

(54) SEALANT TESTING FOR AIRCRAFT FUEL TANKS

(71) Applicant: The Boeing Company, Chicago, IL (US)

(72) Inventors: William J. Sweet, Seattle, WA (US); Kevin R. Housen, Tacoma, WA (US); Jason Scott Damazo, Seattle, WA (US); Arthur C. Day, Seattle, WA (US)

(73) Assignee: The Boeing Company, Chicago, IL (US)

(*) Notice: Subject to any disclaimer, the term of this patent is extended or adjusted under 35 U.S.C. 154(b) by 120 days.

(21) Appl. No.: 14/864,469

(22) Filed: Sep. 24, 2015

(65) Prior Publication Data

US 2017/0089815 A1 Mar. 30, 2017

(51) Int. Cl.
| | |
|---|---|
| *G01B 7/16* | (2006.01) |
| *G01N 3/02* | (2006.01) |
| *B29C 33/12* | (2006.01) |
| *B29C 39/10* | (2006.01) |
| *B64D 37/32* | (2006.01) |

(Continued)

(52) U.S. Cl.
CPC ............. *G01N 3/02* (2013.01); *B29C 33/123* (2013.01); *B29C 39/10* (2013.01); *B64D 37/32* (2013.01); *G01M 7/08* (2013.01); *G01N 3/313* (2013.01); *G01N 3/317* (2013.01); *G01N 27/028* (2013.01); *B29K 2705/00* (2013.01); *G01N 19/04* (2013.01); *G01N 2203/006* (2013.01)

(58) Field of Classification Search
CPC ........ G01N 3/02; G01N 27/028; G01N 3/313; G01N 3/317; B29C 33/123; B29C 39/10; B64D 37/32; G01M 7/08; G01B 3/00

USPC ............................... 73/774; 442/186; 324/72
See application file for complete search history.

(56) References Cited

U.S. PATENT DOCUMENTS 3,219,915 A * 11/1965 Person .................... H01G 4/005
                                                       323/370
3,989,984 A * 11/1976 Amason ................. B29C 70/885
                                                       244/1 A (Continued)

FOREIGN PATENT DOCUMENTS

WO        2014193520 A1     12/2014

OTHER PUBLICATIONS

Sahrim Haji Ahmad; High strain-rate behaviour of polymers using blast-wave and impact loading methods; Dec. 30, 1988; https://dspace.lboro.ac.uk/dspace-jspui/bitstream/2134/7496/3/16568.pdf, entire document.

*Primary Examiner* — Harshad R Patel
*Assistant Examiner* — Octavia Hollington
(74) *Attorney, Agent, or Firm* — Duft Bornsen & Fettig LLP

(57) ABSTRACT

An apparatus and a method for simulating a mechanical stress applied to a sealant from a lightning strike upon an aircraft is provided. The apparatus comprises a specimen, a test fixture, and a capacitor. The specimen comprises an electrically non-conductive sealant for an aircraft fuel tank having a cylindrical shape, and an electrically conductive wire centered axially within the sealant. The test fixture secures the specimen during testing. The capacitor is electrically coupled to the test fixture, and simulates a lightning strike upon the aircraft by vaporizing the wire with a current to generate a mechanical shock to the sealant.

22 Claims, 9 Drawing Sheets

(51) Int. Cl.
*G01M 7/08* (2006.01)
*G01N 27/02* (2006.01)
*G01N 3/313* (2006.01)
*G01N 3/317* (2006.01)
*B29K 705/00* (2006.01)
*G01N 19/04* (2006.01)

(56) References Cited

U.S. PATENT DOCUMENTS

| | | | | |
|---|---|---|---|---|
| 4,328,461 A * | 5/1982 | Butters | ................ | G01R 15/144 |
| | | | | 324/72 |
| 4,448,838 A * | 5/1984 | McClenahan | ........... | B29C 70/08 |
| | | | | 428/408 |
| 7,988,086 B2 * | 8/2011 | Tichborne | .............. | B64D 37/32 |
| | | | | 244/1 A |
| 8,263,864 B2 * | 9/2012 | Orgaz Villegas | ...... | B64D 45/02 |
| | | | | 174/78 |
| 8,717,735 B2 * | 5/2014 | Day | ......................... | F16J 15/14 |
| | | | | 361/218 |
| 9,267,906 B2 * | 2/2016 | Anway | ................ | B29C 65/483 |
| 9,422,622 B2 * | 8/2016 | Storey | ................ | A61N 1/3752 |

\* cited by examiner

FIG. 11

| Sealant & $P_{50}$ | 525V Charge | 550V Charge | 575V Charge | 600V Charge | 625V Charge |
|---|---|---|---|---|---|
| Sealant 1 $P_{50}$ = 13.03J | 12.32J | 13.33J | 14.64J | Materials Not Tested in the Range | |
| | 12.29J | 13.28J | 14.70J | | |
| | 12.29J | 12.38J | 14.60J | | |
| | 12.08J | 13.41J | 14.65J | | |
| | 12.28J | 13.51J | 14.61J | | |
| Sealant 2 $P_{50}$ = 13.30J | 12.41J | 13.43J | 14.67J | | |
| | 12.47J | 13.33J | 14.60J | | |
| | 12.26J | 13.26J | 14.76J | | |
| | 12.51J | 13.39J | 14.68J | | |
| | 12.06J | 13.53J | 14.61J | | |
| Sealant 3 $P_{50}$ = 15.58J | Materials Not Tested in the Range | | 14.69J | 16.02J | 17.31J |
| | | | 14.62J | 15.89J | 16.82J |
| | | | 14.66J | 15.88J | 17.17J |
| | | | 14.80J | 16.10J | 17.38J |
| | | | 14.75J | 16.08J | 17.33J |
| Sealant 4 $P_{50}$ = 14.34J | | 13.76J | 14.69J | 16.15J | |
| | | 13.37J | 15.04J | 15.60J | |
| | | 13.31J | 15.08J | 16.00J | |
| | | 13.63J | 14.75J | 16.00J | |
| | | 13.51J | 14.75J | 16.26J | |
| Sealant 5 $P_{50}$ = 12.05J | 12.31J | 13.65J | 14.81J | Materials Not Tested in the Range | |
| | 11.99J | 13.18J | | | |
| | 12.03J | 13.31J | | | |
| | 12.42J | 13.08J | | | |
| | 11.97J | 13.18J | | | |

▩ Indicates Fail

SEALANT TESTING FOR AIRCRAFT FUEL TANKS

FIELD

This disclosure relates to the field of aircraft, and in particular, to testing the sealants utilized in fuel tanks of aircraft.

BACKGROUND

Aircraft fuel tanks include a number of sections that are secured together with fasteners. The fasteners and the mating surfaces of the tanks are coated with a sealant to ensure that the fuel tanks do not leak. The sealant also forms a mechanical barrier between the fuel in the tanks and electrical arcing that may arise between the fasteners and the sections of the fuel tank if the aircraft is struck by lightning. However, the electrical arcing that may occur during a lightning strike may generate a mechanical stress on the sealant, which may cause the sealant to crack or break, enabling an arc to ignite the fuel. Therefore, the Federal Aviation Administration (FAA) requires that testing be performed to ensure that the sealants used in aircraft fuel tanks are capable of withstanding the stress due to lightning strikes on the aircraft.

Current testing methods for aircraft fuel tanks include assembling a sample of the fasteners and panels used for a fuel tank, and applying a high current through the sample. The current generates arcing around the fasteners, which stresses the sealant applied to the fasteners. The samples are then inspected to determine if breaks or cracks in the sealant are present around the fasteners.

The problem with the current testing method is that assembling the sample is expensive and time consuming. Further, it is difficult to reliably reproduce the electrical arcing around the fasteners from one sample to another, or from one fastener to another in the same sample, due to variations in the mechanical interface between the fasteners and the panels.

Therefore, there is a desire to improve the testing of how sealants utilized for aircraft fuel tanks may respond to lightning strikes upon the aircraft.

SUMMARY

Embodiments described herein provide apparatus and a method for simulating a mechanical stress applied to a sealant from a lightning strike upon an aircraft. A wire embedded in a sample of the sealant is vaporized by a current, which applies a mechanical shock to the sealant that is reproducible from one test to another. The sample may then be inspected for fractures or cracks, which may be indicative of how the sealant may respond to the stress induced by lightning strikes upon an aircraft.

One embodiment comprises a specimen, a test fixture, and a capacitor. The specimen comprises an electrically non-conductive sealant for an aircraft fuel tank having a cylindrical shape, and an electrically conductive wire centered axially within the sealant. The test fixture secures the specimen for testing. The capacitor is electrically coupled to the test fixture, and simulates a lightning strike upon the aircraft by vaporizing the wire with a current to generate a mechanical shock to the sealant.

Another embodiment comprises a method of simulating a mechanical stress applied to a sealant from a lightning strike upon an aircraft. The method comprises fabricating a specimen that comprises an electrically non-conductive sealant for an aircraft fuel tank having a cylindrical shape, and an electrically conductive wire centered axially within the sealant. The method further comprises securing the specimen in a test fixture, and simulating a lightning strike upon the aircraft by vaporizing the wire using a current to generate a mechanical shock to the sealant.

Another embodiment comprises a mold for fabricating a specimen, a test fixture, and a capacitor. The mold enables an electrically conductive wire to be centered axially within a cylindrical cavity of the mold, and receives an electrically non-conductive liquid sealant for an aircraft fuel tank in the cavity. The mold separates along a plane through a long axis of the cylindrical cavity to expel the specimen upon curing the sealant. The test fixture secures the specimen for testing, and the capacitor simulates a lightning strike upon the aircraft by vaporizing the wire within the specimen with a current to generate mechanical shock to the sealant.

The above summary provides a basic understanding of some aspects of the specification. This summary is not an extensive overview of the specification. It is intended to neither identify key or critical elements of the specification nor delineate any scope particular embodiments of the specification, or any scope of the claims. Its sole purpose is to present some concepts of the specification in a simplified form as a prelude to the more detailed description that is presented later.

DESCRIPTION OF THE DRAWINGS

Some embodiments are now described, by way of example only, and with reference to the accompanying drawings. The same reference number represents the same element or the same type of element on all drawings.

FIG. 11 illustrates a table of test results performed on five different sealants in an exemplary embodiment.

DESCRIPTION

The figures and the following description illustrate specific exemplary embodiments. It will thus be appreciated that those skilled in the art will be able to devise various arrangements that, although not explicitly described or shown herein, embody the principles of the embodiments and are included within the scope of the embodiments. Furthermore, any examples described herein are intended to aid in understanding the principles of the embodiments, and are to be construed as being without limitation to such specifically recited examples and conditions. As a result, the inventive concept(s) is not limited to the specific embodiments or examples described below, but by the claims and their equivalents.

Figure 1:
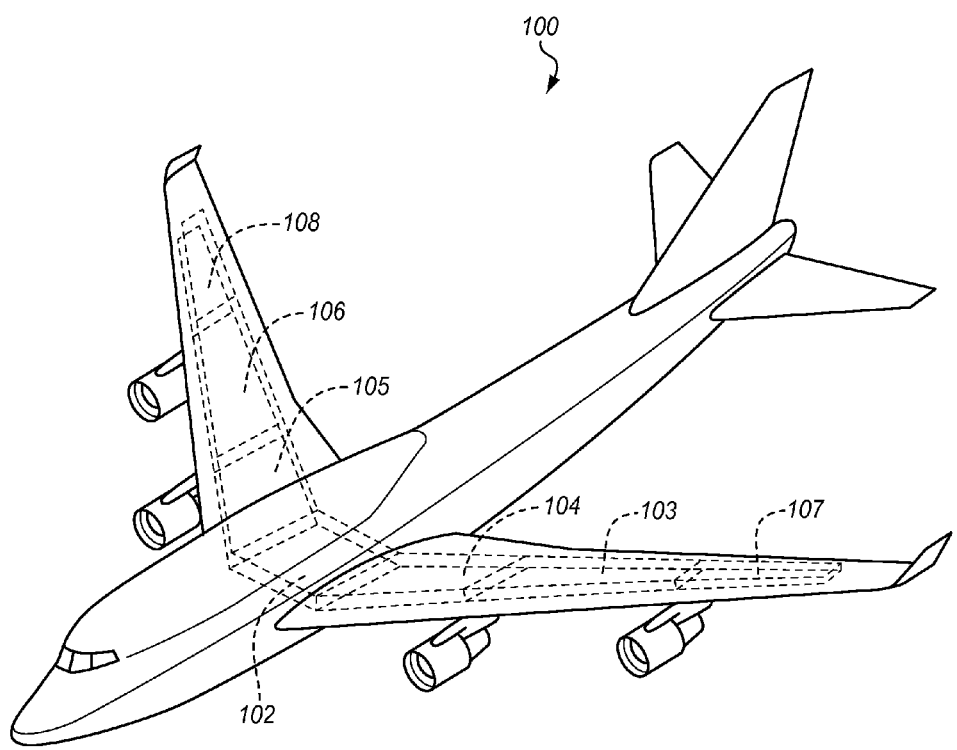
FIG. 1 is an aircraft that utilizes a number of internal fuel tanks in an exemplary embodiment.

FIG. 1 illustrates an aircraft 100 that includes a number of internal fuel tanks 102-108 in an exemplary embodiment. Aircraft 100 may include a center wing tank 102, main tanks 103-106 corresponding to different engines onboard aircraft 100, and reserve tanks 107-108 for an engine on each side of aircraft 100. One purpose of having different tanks onboard aircraft 100 is weight distribution. Fuel is heavy, so multiple tanks ensure that the weight of the fuel is distributed evenly between the different tanks 102-108 onboard aircraft 100. This also enables the center of gravity of aircraft 100 to be controlled as fuel is consumed. For example, the fuel may be re-distributed between tanks 102-108 during flight to enable the weight of the fuel to be distributed evenly. Another purpose of having different tanks onboard aircraft 100 is to ensure that the failure of any one component of the fuel system does not result in the loss of power of more than one engine.

The FAA provides regulations regarding the prevention of fuel vapor ignition in the fuel tanks of aircraft (e.g., fuel tanks 102-108 of aircraft 100), due to direct lightning strikes upon aircraft 100, swept lighting strikes, coronals, and/or streamering. Swept strikes occur when the lightning strike is deformed by the aerodynamic forces on aircraft 100, and may propagate in unusual ways across the airframe of aircraft 100. A coronal is a luminous discharge that occurs as a result of an electrical potential difference between aircraft 100 and the area around aircraft 100. Streamering is a branch-like ionized path that occurs due to direct strikes on aircraft 100 or when lightning is imminent.

The ignition of fuel in tanks 102-108 may occur if the sealant around the various fasteners in tanks 102-108 (not shown) mechanically fails due to stress. For instance, modern aircraft may utilize composite structures to form fuel tanks, which are often panels of carbon fiber and epoxy that are joined together with metal fasteners. While the composite structures have a high electrical resistance, the metal fasteners used to join the panels together may enable high currents from a lighting strike to flow through the fasteners, which may cause arcing between the fasteners and the composite panels. If this arcing fractures the sealant, then the arcing can ignite fuel vapors in the tank. Due to this concern, the FAA has regulations in place that require aircraft manufacturers to perform testing on the sealants that they use to seal fuel tanks onboard their aircraft.

Current lightning testing of aircraft fuel tanks entails assembling a section of composite panels with metal fasteners, and attempting to induce arcing in the fasteners. However, the arcing can be difficult to reproduce between different tests. For instance, if different sealants are being tested for possible use in an aircraft fuel tank, it can be difficult to determine whether variations in the result of the tests are due to the sealants themselves or rather, due to arcing differences between the samples.

The embodiments described herein aim to mitigate these issues utilizing cylindrical samples of sealant that include thin metal wires that when vaporized (e.g., utilizing a high current discharge from a capacitor or a bank of capacitors), applies a mechanical stress to the sealant sample that is both reproducible from one test to another, and quantifiable with respect to the energy deposited into the sample by the wire. The sample may then be inspected for fracture, which when correlated with the energy deposited into the sample, provides information regarding the material performance of the sealant. Further, performing such tests at different temperatures is easier than attempting to place a fastener and panel assembly (which may be large and/or of irregular shape) into an environmental chamber.

Figure 2:
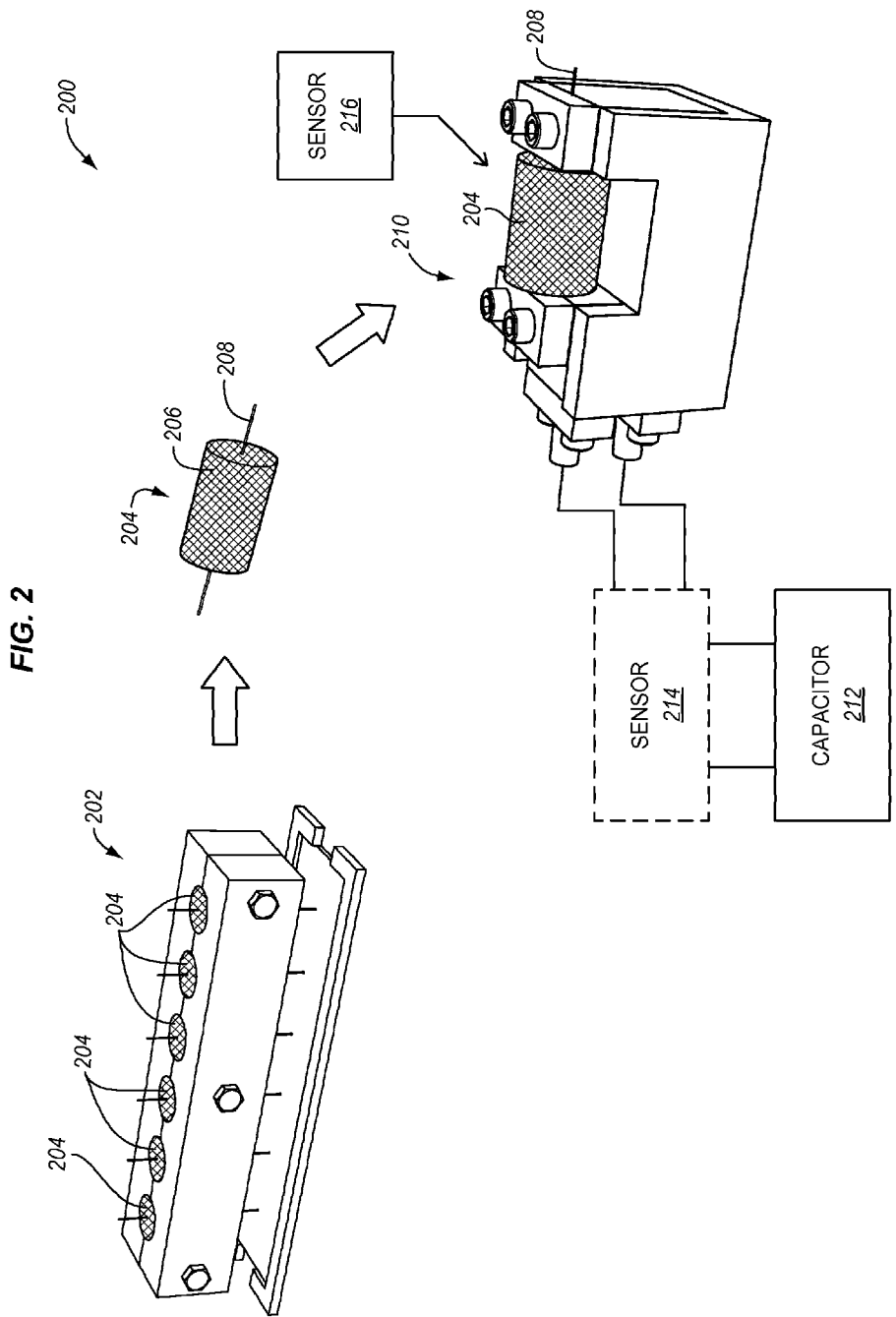
FIG. 2 illustrates a system for simulating a mechanical stress applied to a sealant from a lightning strike upon an aircraft in an exemplary embodiment.

FIG. 2 illustrates a system 200 for simulating a mechanical stress applied to a sealant from a lightning strike upon an aircraft in an exemplary embodiment. In this embodiment, system 200 includes a mold 202, which is utilized to fabricate one or more specimens 204 for stress testing fuel tank sealants. Specimen 204 may then be removed from mold 202. In this embodiment, specimen 204 comprises an electrically non-conductive sealant 206 formed into a shape of a cylinder (e.g., utilizing one or more cavities within mold 202), and an electrically conductive wire 208 that is centered axially within sealant 206.

Specimen 204 may then be place into a test fixture 210, which secures specimen 204 in place. Test fixture 210 also electrically couples wire 208 to one or more capacitors 212, which applies a high current to wire 208 within specimen 204. The current from capacitor 212 vaporizes wire 208, which generates a mechanical shock to sealant 206.

Figure 3A:
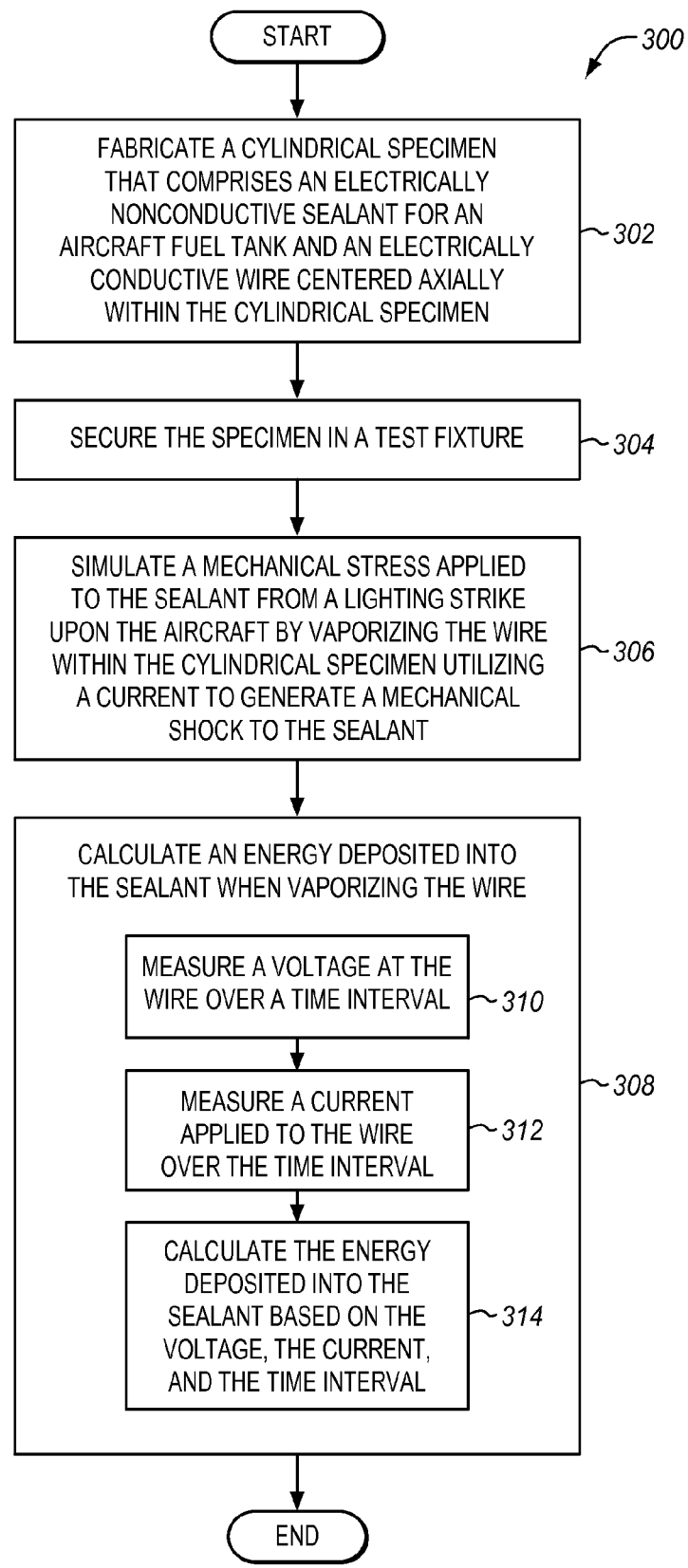
FIGS. 3A-3C are flow charts of a method of simulating a mechanical stress applied to a sealant from a lightning strike upon an aircraft in an exemplary embodiment.
Figure 3B:
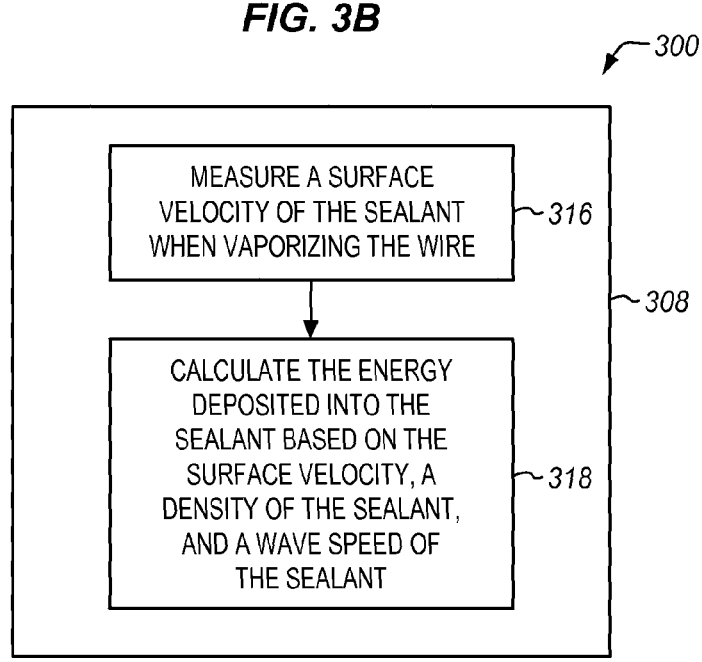
Figure 3C:
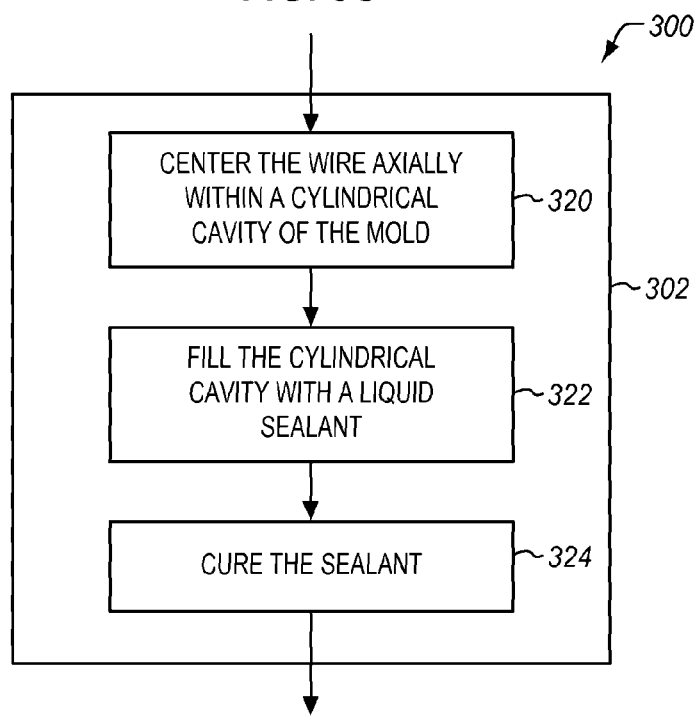

FIGS. 3A-3C are flow charts of a method 300 of simulating a mechanical stress applied to a sealant from a lightning strike upon an aircraft in an exemplary embodiment. Method 300 will be described with respect to system 200, although method 300 may be performed by other systems, not shown. The steps of the flow charts described herein may include other steps, not shown. Also, the steps of the flow charts described herein may be performed in an alternate order.

Figure 4:
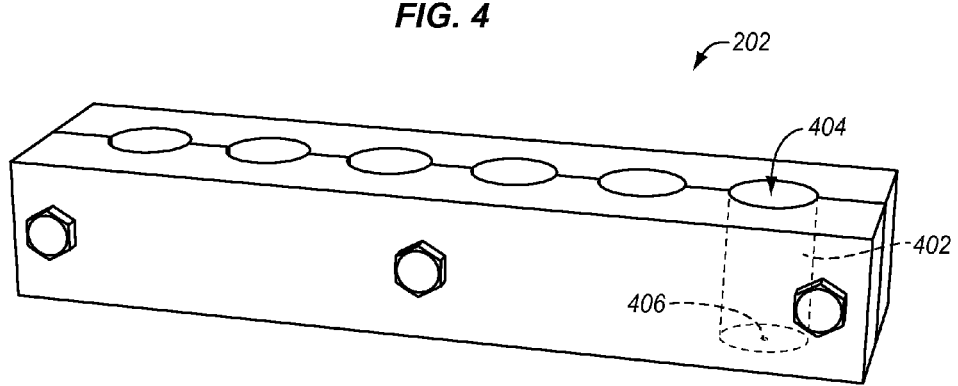
FIG. 4 illustrates a mold including a number of cylindrical cavities in an exemplary embodiment.

In order to perform stress testing on a particular fuel tank sealant (e.g., sealant 206), specimen 204 is fabricated (see step 302). For example, mold 202 may be utilized to fabricate specimen 204. FIG. 4 illustrates mold 202 including a cylindrical cavity 402 in an exemplary embodiment. FIG. 4 illustrates just one possible configuration for mold 202, and other configurations may be utilized as desired. For instance, mold 202 may include more or fewer cavities, may have a different shape or size, may include various features for securing sections of mold 202 together, etc.

In FIG. 4, cavity 402 includes an opening along a top portion 404 and a smaller opening along a bottom portion 406. Top portion 404 is sized to enable sealant 206 to be introduced as a liquid into cavity 402, while bottom portion 406 is sized to both secure wires 208 in place as sealant 206 cures, and to prevent the sealant 206 in its liquid form from draining out of cavity 402.

Figure 5:
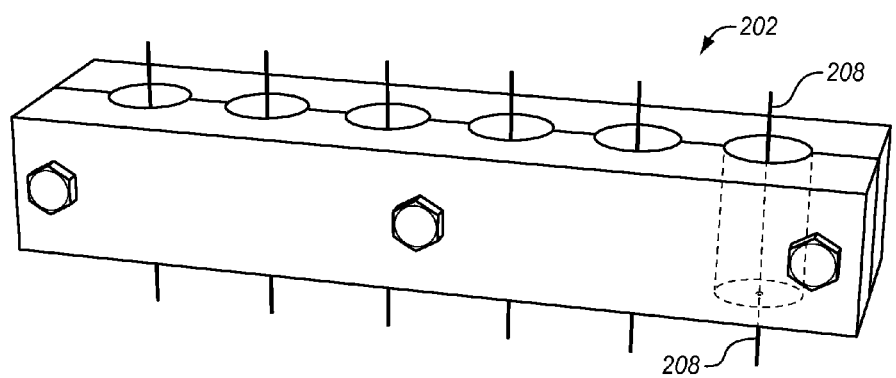
FIGS. 5-7 illustrate different views of a mold during a fabrication process for a specimen of sealant in an exemplary embodiment.
Figure 6:
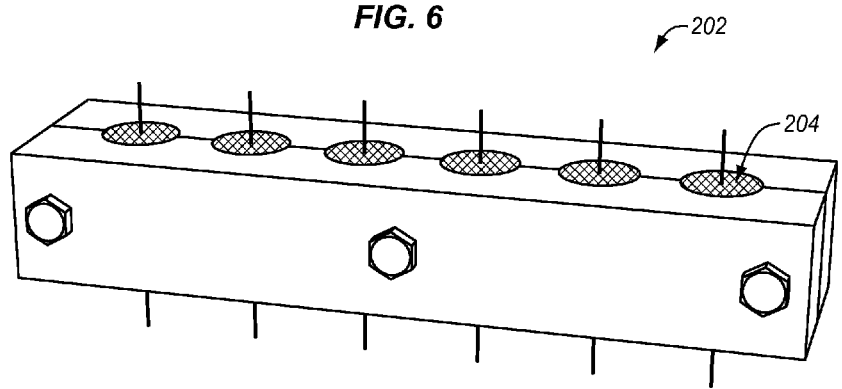
Figure 7:
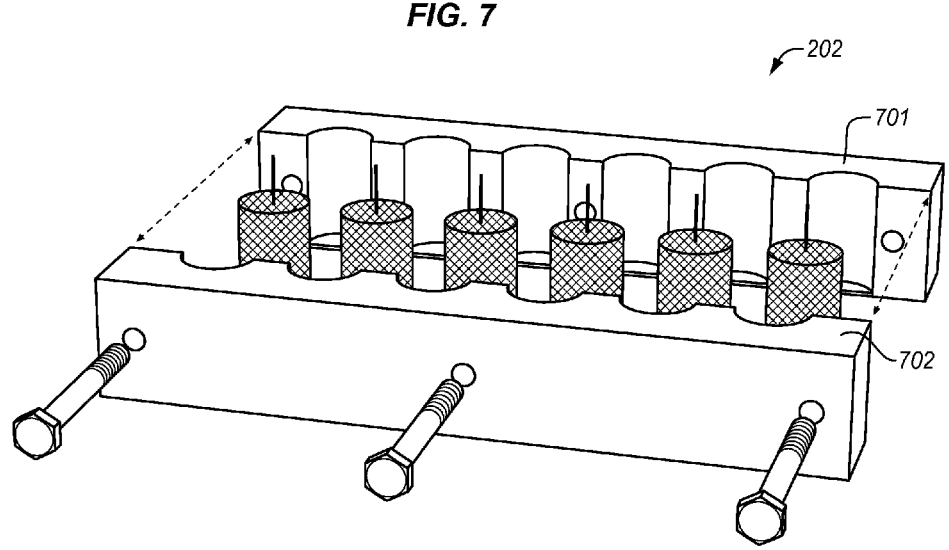

FIGS. 5-7 illustrate different views of mold 202 during a fabrication process for a specimen of sealant in an exemplary embodiment. To fabricate specimen 204, wire 208 may be inserted into cavity 402, which is centered axially within cavity 402 (see FIG. 5 and step 320 of FIG. 3C). Wire 208 may be aluminum or some other type of conductive metal, and is typically thin (e.g., wire 208 may have a diameter between 100 micrometers (μm) and 300 μm). All metals have a specific heat of vaporization enabling more or less energy deposition before vaporization. A metal with a higher heat of vaporization would produce higher stress in specimen 204, and would be appropriate when testing higher strength materials. Therefore, the choice of metal for wire 208 may depend on the type of material being tested.

Sealant 206 in a liquid form may then be introduced into cavity 402 of mold 202 (see step 322 of FIG. 3C), which is enabled to cure or harden (see FIG. 6 and step 324 of FIG. 3C). Upon curing sealant 206, mold 202 is separated into one or more sections 701-702, which enables specimen 204 to be removed from mold 202 (see FIG. 7).

Figure 8:
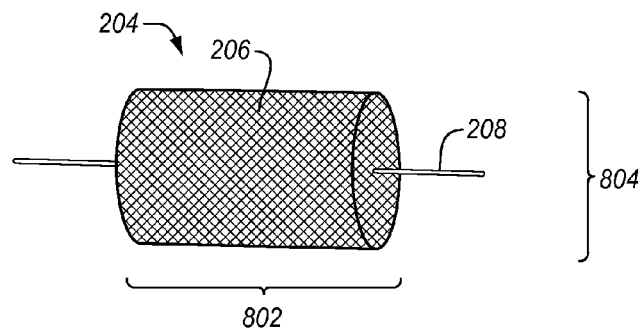
FIG. 8 illustrates a view of a specimen of sealant in an exemplary embodiment.

FIG. 8 illustrates the result of the fabrication process for specimen 204 illustrated in FIGS. 5-7 in an exemplary embodiment. In this view, specimen 204 has a length 802 and a diameter 804 that may change depending upon the type of sealant used in specimen 204, the temperature of the test to perform on specimen 204, etc. For instance, it may be desirable to fabricate specimen 204 to have a larger diameter 804 (e.g., 1½ centimeter (cm)) when sealant 206 is tested at higher temperatures (e.g., above 25 degrees Celsius), since the fracture mechanism of sealant 206 at higher temperatures is more likely to be ductile fracture. It may be desirable to fabricate specimen 204 to have a smaller diameter 804 (e.g., ½ cm) at lower temperatures (e.g., below −20 degrees Celsius), since the fracture mechanism of sealant 206 at lower temperatures is more likely to be brittle fracture. This may be performed by modifying the dimensions of cavity 402 of mold 202.

In response to fabricating specimen 204, specimen 204 is secured in a test fixture (see step 304 of method 300). For instance, specimen 204 may be secured into test fixture 210 of FIG. 2.

Figure 9:
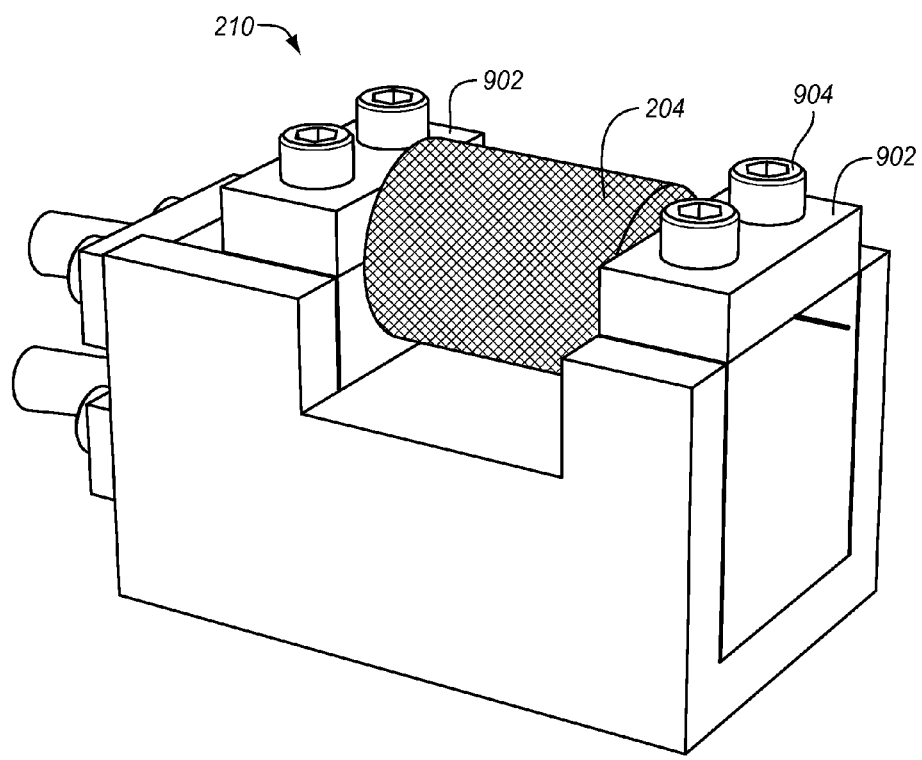
FIG. 9 is a view of a test fixture in an exemplary embodiment.

FIG. 9 is a view of test fixture 210 in an exemplary embodiment. FIG. 9 illustrates just one possible configuration for test fixture 210, and other configurations, not shown, may exist. In this view, specimen 204 is mounted to test fixture 210 between conductive clamps 902, which enables wire 208 of specimen 204 to be electrically connected to capacitor 212. Clamps 902 also secures specimen 204 in place. When capacitor 212 is electrically coupled to wire 208, capacitor 212 discharges a current through wire 208 and vaporizes wire 208. Vaporizing wire 208 simulates a mechanical stress applied to sealant 206 from a lightning strike upon an aircraft by generating a mechanical shock to sealant 206 (see step 306 of method 300).

The mechanical shock applied to sealant 206 by vaporizing wire 208 varies based on a number of factors, including the capacitance of capacitor 212 and the voltage of capacitor 212. Measuring the amount of energy deposited into sealant 206 of specimen 204 (e.g., utilizing sensor 214 and/or sensor 216) can help quantify the energy deposited into sealant 206.

The energy deposited into sealant 206 utilizing system 200 is controllable over a number of tests, and is based on a combination of the voltage and the capacitance of capacitor 212. In some embodiments, the energy deposited into sealant 206 by vaporizing wire 208 may be measured by sensor 214 and/or sensor 216 (see step 308 of FIG. 3). For instance, sensor 214 may measure the voltage at wire 208 over a time interval (see step 310 of FIG. 3A) and the current applied to wire 208 over the time interval (see step 312), which enables sensor 214 to calculate the energy deposited. The energy deposited may also vary over time. The cumulative energy deposition may be calculated from voltage and current measurements by following formula: $J_{cum}\int IV \, \Delta t$, where the cumulative energy in joules ($J_{cum}$) is the integral of the current (I) multiplied by the voltage (V) multiplied by delta time ($\Delta t$).

However, measuring the current applied to wire 208 and the voltage applied to wire 208 is just one possible mechanism for calculating the energy deposited into sealant 206 from vaporizing wire 208. For example, sensor 216 (see FIG. 2) may comprise a Velocity Interferometer System for Any Reflector (VISAR), which could be used to measure the surface velocity of sealant 206 when vaporizing wire 208 (see step 316 of FIG. 3B). The surface velocity along with the density and wave speed of sealant 206 can be used to calculate and quantify the shock related stress caused when wire 208 vaporizes (see step 318 of FIG. 3B). The stress may be calculated by the following formula: $\sigma = \frac{1}{2} \rho c v_s$, where the stress ($\sigma$) is 0.5 times the density ($\rho$) of sealant 206 times the wave speed (c) of sealant 206 times the measured surface velocity ($v_s$) of sealant 206.

In some embodiments, wire 208 may not extend outside the ends of specimen 204, but instead may be encapsulated within sealant 206. In these embodiments, wire 208 is coupled to a pair of thicker electrodes, each of which extends from the ends of specimen 204. The thicker electrodes are then mounted in test fixture 210 in a manner similar to wire 208. This may provide advantages by ensuring that the energy utilized to vaporize wire 208 is encapsulated within sealant 206, instead of some of the energy being used to vaporize portions of wire 208 that are outside of sealant 206.

Figure 10:
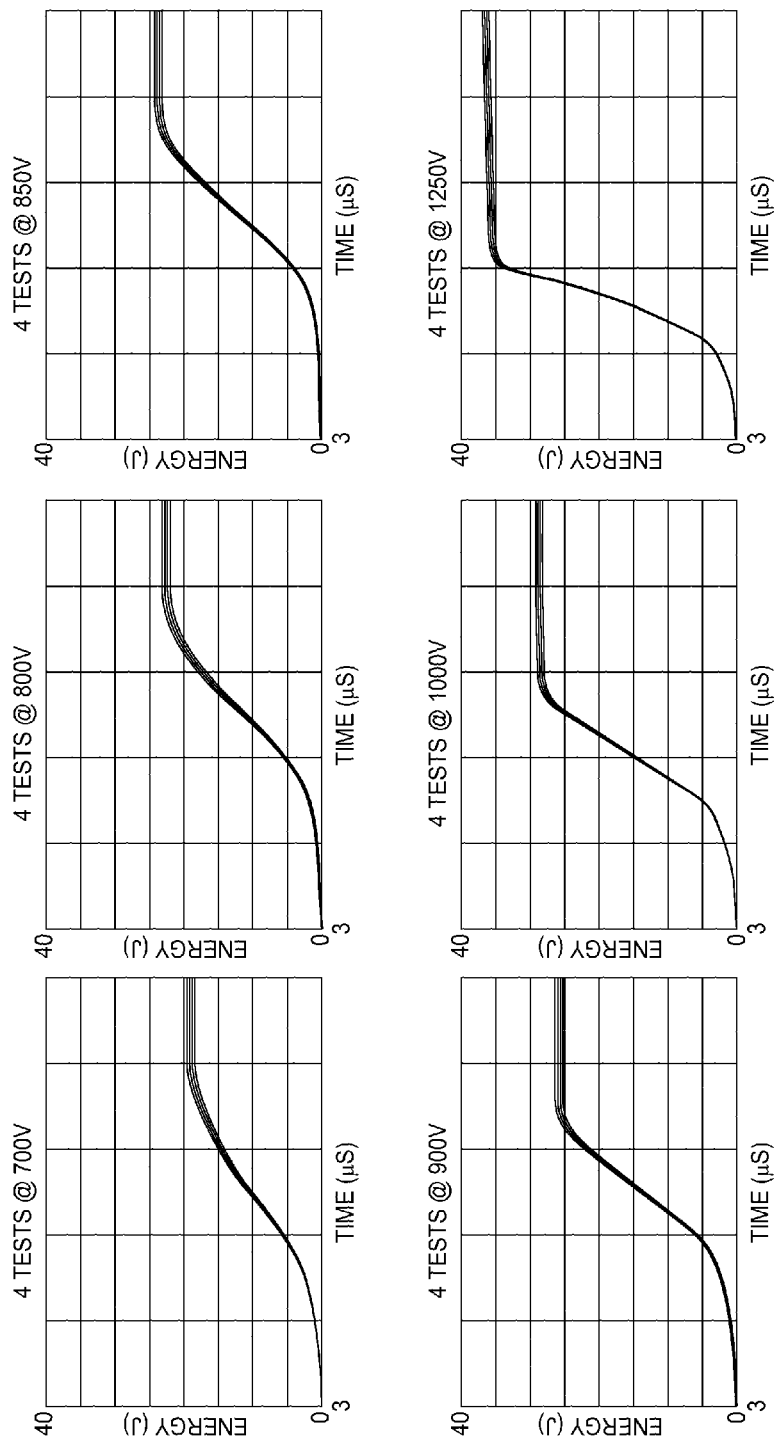
FIG. 10 illustrates the results of specimen tests in an exemplary embodiment.

As discussed previously, it is advantageous that stress testing fuel tank sealants is reproducible over a number of tests, as this is one problem with current testing methods that utilize fastener and panel assemblies to represent a fuel tank. Tests were performed to determine how reproducible the testing of fuel tanks sealants is utilizing system 200, or systems similar to system 200. FIG. 10 illustrates the results of specimen tests in an exemplary embodiment. The tests were performed utilizing a capacitor bank having a capacitance of 222μ Farad (μF) and a voltage between 700 Volts (V) and 1250V @ 71 Celsius. For these tests, the specimens were cylindrical specimens 2.54 cm long and 1 cm in diameter. Each specimen included a 250 μm aluminum wire aligned axially within the specimen. Each test utilized the same type of fuel tank sealant.

Four tests were performed at each voltage on the specimens, and the energy deposition was measured. FIG. 10 illustrates that in each case, the energy deposition varied little from one test to another. This ensures that variations in the results of the tests (e.g., determining whether the specimens fractured or did not fracture) are not due to differences in the energy deposition within the same testing group (e.g., specimens in the 700V group).

FIG. 11 illustrates a table 1100 of test results performed on five different sealants in an exemplary embodiment. The table 1100 was generated utilizing specimens at −40 C, with an aluminum wire having a diameter of 250 μm and a length of 28 millimeters.

To generate table 1100, tests were performed at 525V, 550V, 575V, 600V, and 625V, although not all sealants were tested at each of these voltages. Table 1100 also shows, in the left column, the calculated $P_{50}$ for each sealant type that was tested. The $P_{50}$ is calculated using a logistic regression algorithm and represents the energy at which you should expect 50% of the specimens to fail. For example, the $P_{50}$ for sealant #1 is 13.03 J. In contrast, the $P_{50}$ for sealant #3 failed at 15.58 J. Using table 1100, it is possible to characterize how different sealants respond to stress, thereby enabling a determination of which sealants may perform better in response to lighting events for aircraft.

In some cases, it may be desirable to perform tests of specimens at different temperatures, as discussed previously, to determine whether a particular type of sealant is capable of resisting either brittle fracture or ductile fracture over a variety of temperatures. This type of testing ensures that variations in temperatures that may arise within a fuel tank do not negatively impact the mechanical strength of sealants used in the fuel tanks if a lightning event were to occur. These types of tests can be performed more easily in an environmental chamber utilizing the specimens discussed herein than would be possible if a fastener and panel assembly were used for testing.

Further, although the embodiments described herein refer to testing sealants for aircraft fuel tanks, other materials may be tested as desired. In this regard, any material that may be hardened or cured around an electrically conductive wire may be utilized for testing the response of the material to mechanical stress.

Utilizing the systems and method discussed herein for simulating a mechanical stress applied to a sealant from a lightning strike upon an aircraft, different sealants can be quickly and accurately characterized with regard to their capabilities. This type of testing also enables the aircraft manufacturer to accelerate the sealant development process and ensure compliance with FAA regulations regarding fuel tank sealants utilized onboard their aircraft.

Although specific embodiments were described herein, the scope is not limited to those specific embodiments. Rather, the scope is defined by the following claims and any equivalents thereof.

The invention claimed is:

1. A system comprising:
a specimen, comprising:
an electrically non-conductive sealant for a fuel tank of an aircraft having a cylindrical shape; and
an electrically conductive wire centered axially within the sealant;
a test fixture configured to secure the specimen during testing;
a capacitor electrically coupled to the test fixture that is configured to simulate a lightning strike upon the aircraft by vaporizing the wire with a current to generate a mechanical shock to the sealant; and
a sensor configured to measure a voltage at the wire over a time interval, to measure the current applied by the capacitor to the wire over the time interval, and to calculate an energy deposited into the sealant when vaporizing the wire based on the voltage, the current, and the time interval.

2. The system of claim 1 wherein:
the wire has exposed portions proximate to ends of the sealant that electrically couple the specimen to the test fixture.

3. The system of claim 1 wherein:
the wire has a diameter between 100 μm and 300 μm.

4. The system of claim 3 wherein:
the wire comprises aluminum.

5. A method, comprising:
fabricating a specimen that comprises an electrically non-conductive sealant for a fuel tank of an aircraft and an electrically conductive wire centered axially within the sealant, wherein the sealant has a cylindrical shape;
securing the specimen in a test fixture;
simulating a lightning strike upon the aircraft by vaporizing the wire with a current to generate a mechanical shock to the sealant; and
calculating an energy deposited into the sealant when vaporizing the wire by:
measuring a voltage at the wire over a time interval;
measuring the current applied to the wire over the time interval; and
calculating the energy deposited into the sealant based on the voltage, the current, and the time interval.

6. The method of claim 5 wherein:
the wire has a diameter between 100 μm and 300 μm.

7. The method of claim 6 wherein:
the wire comprises aluminum.

8. The method of claim 5 wherein fabricating the specimen further comprises:
centering the wire axially within a cylindrical cavity of a mold;
filling the cylindrical cavity with liquid sealant; and
curing the liquid sealant.

9. A system, comprising:
a mold for fabricating a specimen, the mold configured to center an electrically conductive wire axially within a cylindrical cavity of the mold, and to receive an electrically non-conductive liquid sealant for a fuel tank of an aircraft within the cylindrical cavity;
the mold configured to separate along a plane through a long axis of the cylindrical cavity to expel the specimen upon curing the sealant;
a test fixture configured to secure the specimen during testing;
a capacitor electrically coupled to the test fixture that is configured to simulate a lightning strike upon the aircraft by vaporizing the wire with a current to generate a mechanical shock to the sealant; and
a sensor configured to measure a voltage at the wire or a time interval, to measure the current applied by the capacitor to the wire over the time interval, and to calculate an energy deposited into the sealant based on the voltage, the current, and the time interval.

10. The system of claim 9 wherein:
the wire has a diameter between 100 μm and 300 μm.

11. The system of claim 9 wherein:
the wire has exposed portions proximate to ends of the sealant that electrically couple the specimen to the test fixture.

12. A system comprising:
a specimen, comprising:
an electrically non-conductive sealant for a fuel tank of an aircraft having a cylindrical shape; and
an electrically conductive wire centered axially within the sealant;
a test fixture configured to secure the specimen during testing;
a capacitor electrically coupled to the test fixture that is configured to simulate a lightning strike upon the aircraft by vaporizing the wire with a current to generate a mechanical shock to the sealant; and
a sensor configured to measure a surface velocity of the sealant when vaporizing the wire, and to calculate an energy deposited into the sealant when vaporizing the wire based on the surface velocity, a density of the sealant, and a wave speed of the sealant.

13. The system of claim 12 wherein:
the wire has exposed portions proximate to ends of the sealant that electrically couple the specimen to the test fixture.

14. The system of claim 12 wherein:
the wire has a diameter between 100 μm and 300 μm.

15. The system of claim 14 wherein:
the wire comprises aluminum.

16. A method, comprising:
fabricating a specimen that comprises an electrically non-conductive sealant for a fuel tank of an aircraft and an electrically conductive wire centered axially within the sealant, wherein the sealant has a cylindrical shape;
securing the specimen in a test fixture;
simulating a lightning strike upon the aircraft by vaporizing the wire with a current to generate a mechanical shock to the sealant; and calculating an energy deposited into the sealant when vaporizing the wire by:
  measuring a surface velocity of the sealant when vaporizing the wire; and
  calculating the energy deposited into the sealant based on the surface velocity, a density of the sealant, and a wave speed of the sealant.

17. The method of claim 16 wherein:
the wire has a diameter between 100 μm and 300 μm.

18. The method of claim 17 wherein:
the wire comprises aluminum.

19. The method of claim 16 wherein fabricating the specimen further comprises:
centering the wire axially within a cylindrical cavity of a mold;
filling the cylindrical cavity with liquid sealant; and
curing the liquid sealant.

20. A system, comprising:
a mold for fabricating a specimen, the mold configured to center an electrically conductive wire axially within a cylindrical cavity of the mold, and to receive an electrically non-conductive liquid sealant for a fuel tank of an aircraft within the cylindrical cavity;
the mold configured to separate along a plane through a long axis of the cylindrical cavity to expel the specimen upon curing the sealant;
a test fixture configured to secure the specimen during testing;
a capacitor electrically coupled to the test fixture that is configured to simulate a lightning strike upon the aircraft by vaporizing the wire with a current to generate a mechanical shock to the sealant; and
a sensor configured to measure a surface velocity of the sealant when vaporizing the wire, and to calculate an energy deposited into the sealant when vaporizing the wire based on the surface velocity, a density of the sealant, and a wave speed of the sealant.

21. The system of claim 20 wherein:
the wire has a diameter between 100 μm and 300 μm.

22. The system of claim 20 wherein:
the wire has exposed portions proximate to ends of the sealant that electrically couple the specimen to the test fixture.

* * * * *